United States Patent [19]

Leslie

[11] Patent Number: 4,938,582
[45] Date of Patent: Jul. 3, 1990

[54] CHROMO THERAPY DEVICE

[76] Inventor: Michael J. Leslie, 99 Mary Street, Cygnet, Tasmania, Australia

[21] Appl. No.: 288,982

[22] Filed: Dec. 22, 1988

[30] Foreign Application Priority Data

Dec. 24, 1987 [AU] Australia .................... PI6092

[51] Int. Cl.⁵ ............................. G02C 1/00
[52] U.S. Cl. ............................. 351/158; 351/41
[58] Field of Search .................... 351/41, 158; 362/103

[56] References Cited
U.S. PATENT DOCUMENTS 3,612,651 10/1971 McCurdy ................. 351/158
4,396,259 8/1983 Miller ..................... 351/158

Primary Examiner—Rodney B. Bovernick
Attorney, Agent, or Firm—McAulay Fisher Nissen & Goldberg

[57] ABSTRACT

A chromo therapy device comprises a shade in the form of glasses worn by the user. The glasses are opaque and virtually exclude all light. Various colored lights are fitted to shine onto the inside surface of the shade so that by selecting the desired color of light, this passive use of color produces a relaxed stress-free environment for people with both physiological and psychological symptoms.

16 Claims, 3 Drawing Sheets

CHROMO THERAPY DEVICE

This invention relates to the field of chromo therapy, and is particularly directed to a device in which chromo therapy can be applied to a number of ailments found to be brought on by stress.

BACKGROUND OF THE INVENTION

Chromo therapy is a widely recognized medical phenomenon with the emphasis on the more passive use of colour in setting relaxed, stress-free environments for people with both physiological and psychological symptoms.

A number of ailments brought on by stress include high blood pressure, lack of energy, nervous exhaustion, indigestion, headaches, acidity and inflatulence as well as many other conditions.

Interior designers recognize the use of colour to "set the mood", e.g. relaxed and warm, cool and easy, austere and formal, all reflecting the use of colour to achieve a particular physical and mental response with visual colour stimulation.

In U.S. Pat. No. 4,620,791 there is disclosed a light processor of white and coloured light, whereby white light can be processed into various colours and which may be used for audio-visual therapy, biological experimentation, voice control of speech by colour display, optical logical processing. The white light is processed by dichroic mirrors and liquid crystal cells to produce the desired colours.

Thus it is known that direct stimulation of the retina with certain light frequencies, (colours) effects the central nervous system's balance and harmony giving acknowledged and predictable physiological and psychological responses.

It is an object of this invention to provide a device which is a drug-free approach to the relief of stress through the scientific application of colour, known as chromo therapy.

BRIEF STATEMENT OF THE INVENTION

Thus there is provided according to the invention a chromo therapy device, the device including a shade or the like to be fitted to the head to virtually exclude substantially all light from the eyes, and positioned in front of the eyes, and means within the device to provide a selected colour on the shade so that the retina is stimulated with the desired light frequencies.

BRIEF DESCRIPTION OF THE DRAWINGS

In order to more fully describe the invention reference will now be made to the accompanying drawings in which.

DESCRIPTION OF THE PREFERRED EMBODIMENT

Figure 1:
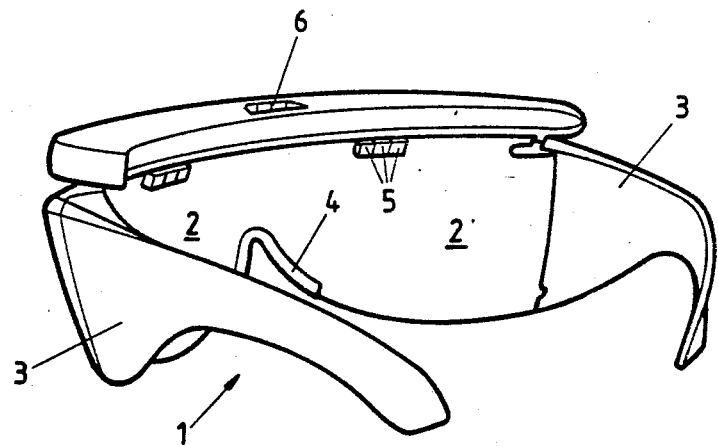
FIG. 1 is a perspective view of one form of the invention.

Referring to the drawing, the invention comprises a unit 1 in the form of a pair of sun-glasses or safety goggles but with all portions thereof being of opaque material so that by its shape virtually all light is excluded from entering the eyes.

The internal surface of the device is preferably of white colouring and preferably of a matt non-reflective material, or could be of a material which is slightly diffusing to spread the light which impinges thereon evenly all over the internal surface, similar to that used for a visual projection screen.

The unit thus includes what could be eye pieces 2 and wings 3 so that these can then be fitted over the ears of the user, there being the usual nose piece 4. On top of the eye pieces 2 or incorporated into the upper surface thereof there can be a plurality of light emitting diodes 5 there being one set of these for each of the eyes.

The light emitting diodes can be one each of the three colours, yellow, green and red and selected ones of these can be selected by touch controls 6 to either switch the unit on and also to select the various colours.

Incorporated in the unit there can be a battery and the desired circuitry as required.

As shown in the diodes are so positioned as to shine the light onto the eye piece, the light being spread to cover the area which would be viewed by the eye, so that in use the eye would only see the desired colour.

Figure 2:
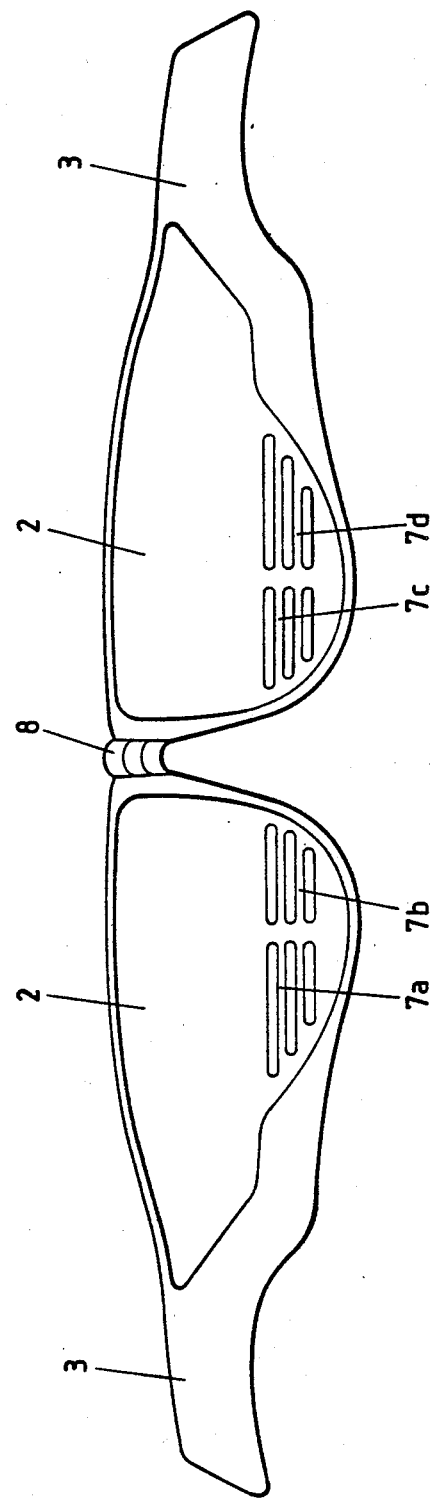
FIG. 2 is a front view of another form of the invention.

In FIG. 2 there is shown a further form of the invention, in which the switches 7 which are soft touch ribbed switches are provided on the front of the eye pieces 2, there being two switches 7a and 7b on one eye piece, and two switches 7c and 7d on the other eye piece. Two of the switches on one eye piece control two of the colours, while on the other eye piece one switch controls the third colour while the remaining switch is a reset switch.

In this embodiment the light emitting diodes are situated on the top inside portion of each eye piece, and the batteries can be incorporated into the top of the eye piece. Also the device can be hinged at 8 so that it can be folded for storage in a box.

Figure 3:
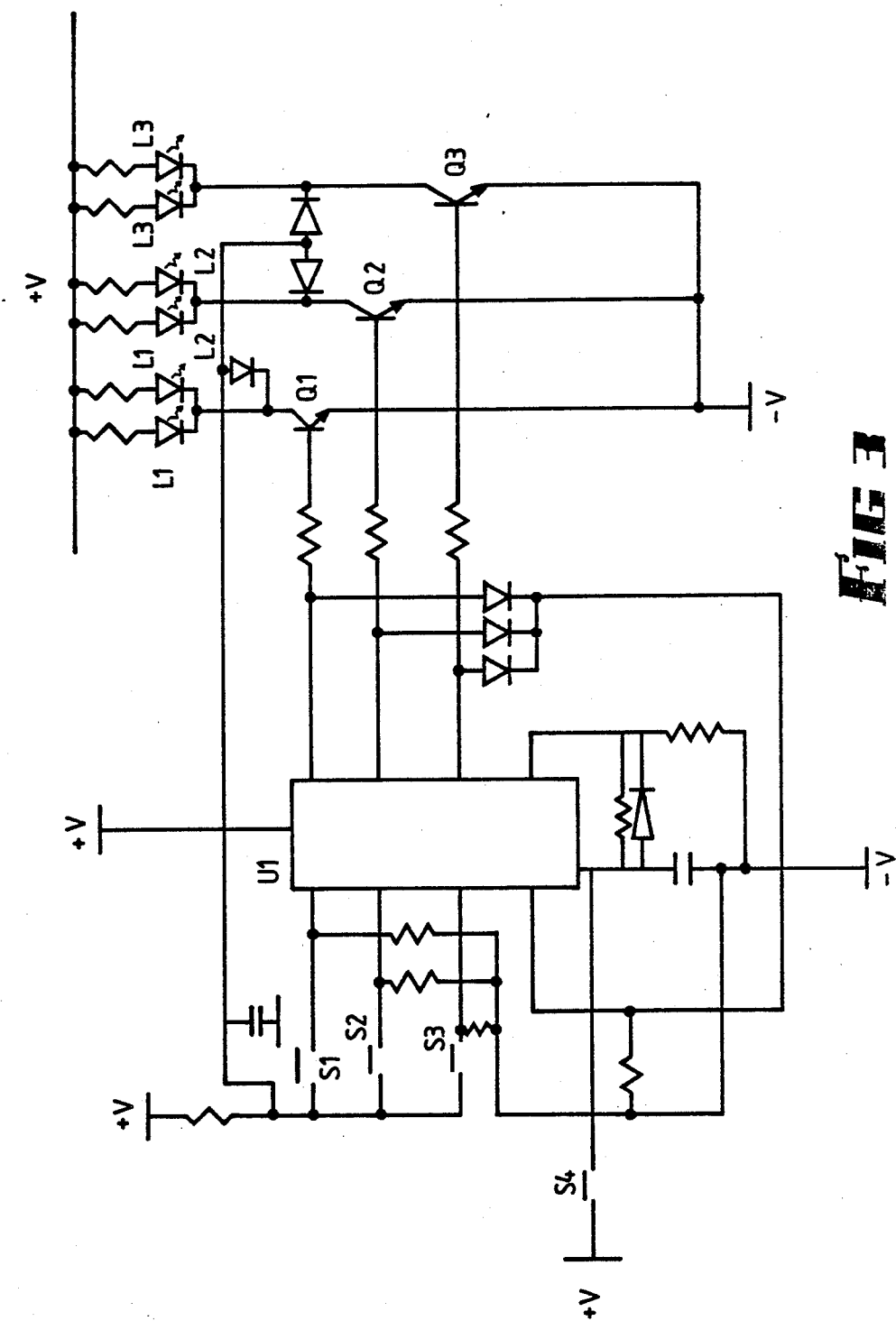
FIG. 3 shows an electrical circuit.

FIG. 3 shows an example of an electrical circuit, it being realised that this shows three pairs of light emitting diodes, L1, L2 and L3, while in practice a circuit would be divided and connected across the hinge to have two sets of lights L1, L2 and L3.

The switches S1, S2 and S3 control respectively the lights L1, L2 and L3, while switch S4 is a reset switch. Also it will be seen that the switches are connected to the chip U1, and the transistors Q1, Q2 and Q3 control the respective lights L1, L2 and L3.

The unit thus can generate one of three colours as selected for a controlled time for the release of stress symptoms. Thus for example, yellow reduces indigestion, reduces nervous fatigue and increases metabolism energy levels. If a green light is used it reduces blood pressure, reduces heart stress, lowers stress headache symptoms, improves concentration and reduces cold symptoms. While red, on the other hand, raises the metabolism rates, increases would healing rates, improves circulation and assists to induce weight loss.

The unit being constructed of solid-state components gives reliability of performance and colour optics of quality and purity and the light levels chosen are based on optometrical standards relating to light intensity and retina response parameters.

It will be realized that the light emitting diodes can be incorporated into the top portion of the unit thus shining through the lower portion of the unit instead of being situated as shown.

It is to be realized that the invention is not limited to the three colours described above, but can utilize other colours. Also the unit may use other light sources. For example a rotating disc having segments of various colours can be used, and also the light can be transmitted from the light source through fibre optics to shine onto the opaque shade area. Also the light unit can be fitted with or incorporated into a reflector to more evenly spread the light in front of each eye. Also, more than one light of each colour could be used to achieve more even spread of light.

Thus it will be seen that by the use of the present unit, the results are achieved with a solid-state precision, and in a more focused and personally suited way so that the therapy can be carried out on a purely individual basis.

Although one form of the invention has been described in some detail it is to be realized that the invention is not to be limited thereto but can include various modifications falling within the spirit and scope of the invention.

The claims defining the invention are as follows:

I claim:

1. A chromo therapy device ot stimulate the retina of the eye with certain light frequencies, said device comprising
   a plurality of light emitting diodes each emitting a different light frequency to project their light onto a screen in front of the eyes, and
   means to select the light frequency depending on the therapy required, said screen being worn by the user and positioned immediately in front of the eyes to exclude ambient light thereform.

2. A chromo therapy device to stimulate the retina of the eyes with a desired light frequency,
   said device being in the form of spectacles with side wings to exclude virtually all ambient light, the area in front of the eyes being in the form of a screen;
   a plurality of light emitting diodes on the upper portion of the device to project a selected frequency of light onto said screen; and
   switch means on said device for selecting the desired light frequency.

3. The chromo therapy device as claimed in claim 2, wherein said device is in the form of sun glasses and is of opaque material.

4. The chromo therapy device as claimed in claim 2, wherein the internal surface of the device is of matt non-reflective material.

5. The chromo therapy device as claimed in claim 1, wherein the internal surface of the device is of a material which is slightly diffusing to spread the light which impinges evenly and over said internal surface.

6. The chromo therapy device as claimed in claim 1, wherein said device is in the form of sun glasses having a set of eyepieces, at least two of each of said light emitting diodes is associated with each of said eyepieces, and said light frequency selection means being associated with said light emitting diodes.

7. The chromo therapy device as claimed in claim 4, wherein said device is in the form of sun glasses and is of opaque material.

8. The chromo therapy device as claimed in claim 6, wherein the internal surface of the device is of matt non-reflective material.

9. The chromo therapy device as claimed in claim 8, wherein said device is formed of opaque material.

10. The chromo therapy device as claimed in claim 2, wherein said device is formed of opaque material.

11. The chromo therapy device as claimed in claim 2, wherein the internal surface of the device is of matt non-reflective material.

12. The chromo therapy device as claimed in claim 2, wherein the internal surface of the device is of a material which is slightly diffusing to spread the light which impinges evenly and over said internal surface.

13. The chromo therapy device as claimed in claim 10, wherein the internal surface of the device is of matt non-reflective material.

14. The chromo therapy device as claimed in claim 13, wherein the internal surface of the device is of a material which is slightly diffusing to spread the light which impinges evenly and over said internal surface.

15. The chromo therapy device as claimed in claim 2, wherein at least two each of said light emitting diodes is associated with each of the eyepieces of the spectacles and said switch means.

16. The chromo therapy device as claimed in claim 14, wherein at least two each of said light emitting diodes is associated with each of the eyepieces of the spectacles and said switch means.

* * * * *